US009901584B2

(12) United States Patent
Wei et al.

(10) Patent No.: US 9,901,584 B2
(45) Date of Patent: Feb. 27, 2018

(54) METHODS OF COSMETICALLY TREATING SKIN CONDITIONS WITH A COSMETIC PERSONAL CLEANSING COMPOSITION

(71) Applicant: The Procter & Gamble Company, Cincinnati, OH (US)

(72) Inventors: Karl Shiqing Wei, Mason, OH (US); Jason Edward Cook, Anderson Township, OH (US); Kevin John Mills, Goshen, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/147,946

(22) Filed: May 6, 2016

(65) Prior Publication Data
US 2016/0324869 A1    Nov. 10, 2016

Related U.S. Application Data

(60) Provisional application No. 62/157,628, filed on May 6, 2015.

(51) Int. Cl.
| | | |
|---|---|---|
| A61K 31/555 | (2006.01) | |
| A61K 8/27 | (2006.01) | |
| A61K 8/31 | (2006.01) | |
| A61K 8/44 | (2006.01) | |
| A61K 8/46 | (2006.01) | |
| A61K 8/49 | (2006.01) | |
| A61K 8/81 | (2006.01) | |
| A61Q 19/00 | (2006.01) | |
| A61Q 19/10 | (2006.01) | |
| A61K 8/03 | (2006.01) | |
| A61K 47/06 | (2006.01) | |
| A61K 47/14 | (2017.01) | |
| A61K 47/36 | (2006.01) | |

(52) U.S. Cl.
CPC .............. *A61K 31/555* (2013.01); *A61K 8/03* (2013.01); *A61K 8/27* (2013.01); *A61K 8/31* (2013.01); *A61K 8/44* (2013.01); *A61K 8/466* (2013.01); *A61K 8/4933* (2013.01); *A61K 8/8152* (2013.01); *A61K 47/06* (2013.01); *A61K 47/14* (2013.01); *A61K 47/36* (2013.01); *A61Q 19/007* (2013.01); *A61Q 19/10* (2013.01); *A61K 2800/548* (2013.01); *A61K 2800/58* (2013.01)

(58) Field of Classification Search
USPC .................. 514/63, 547, 552, 762
See application file for complete search history.

(56) References Cited

U.S. PATENT DOCUMENTS

| | | | |
|---|---|---|---|
| 3,235,455 A | 2/1966 | Judge et al. | |
| 3,281,366 A | 10/1966 | Judge et al. | |
| 3,725,547 A | 4/1973 | Kooistra | |
| 4,161,526 A | 7/1979 | Gorman | |
| 4,345,080 A | 8/1982 | Bolich, Jr. | |
| 4,379,753 A | 4/1983 | Bolich, Jr. | |
| 4,565,693 A | 1/1986 | Marschner | |
| 4,708,863 A | 11/1987 | Bews et al. | |
| 5,037,818 A | 8/1991 | Sime | |
| 5,104,645 A | 4/1992 | Cardin et al. | |
| 5,540,860 A | 7/1996 | Hosseini et al. | |
| 5,573,699 A | 11/1996 | Jones et al. | |
| 5,612,301 A | 3/1997 | Inman | |
| 5,834,409 A | 11/1998 | Ramachandran et al. | |
| 5,886,031 A | 3/1999 | Shin et al. | |
| 6,015,547 A | 1/2000 | Yam | |
| 6,017,562 A | 1/2000 | Kaufman et al. | |
| 6,017,936 A | 1/2000 | Polson et al. | |
| 6,096,297 A | 8/2000 | Jones et al. | |
| 6,162,446 A | 12/2000 | Hani et al. | |
| 6,214,363 B1 | 4/2001 | Beerse et al. | |
| 6,242,007 B1 | 6/2001 | Mohseni et al. | |
| 6,277,360 B1 | 8/2001 | Carew et al. | |
| 6,432,432 B1 | 8/2002 | Mohseni et al. | |
| 6,451,300 B1 | 9/2002 | Dunlop et al. | |
| 6,465,015 B1 | 10/2002 | Mohseni et al. | |
| 6,649,155 B1 | 11/2003 | Dunlop et al. | |
| 6,673,756 B2 | 1/2004 | Sonnenberg et al. | |
| 6,682,724 B2 | 1/2004 | Mohseni et al. | |
| 6,887,859 B2 | 5/2005 | Clapp et al. | |
| 6,974,569 B2 | 12/2005 | Dunlop et al. | |
| 7,026,308 B1 * | 4/2006 | Gavin .................... | A01N 43/40 424/401 |
| 7,381,415 B2 | 6/2008 | Yokoyama et al. | |
| 7,544,367 B2 | 6/2009 | Mohseni et al. | |
| 7,674,785 B2 | 3/2010 | Gavin et al. | |

(Continued)

FOREIGN PATENT DOCUMENTS

| | | |
|---|---|---|
| DE | 195 37 509 A1 | 4/1997 |
| EP | 0034385 A2 | 8/1981 |

(Continued)

OTHER PUBLICATIONS

International Search Report and Written Opinion of the International Searching Authority dated Jul. 29, 2016, PCT/US2016/031078, 15 pages.
International Search Report PCT/US2012/050882 and Written Opinion of the International Searching Authority dated Feb. 7, 2014, 11 pages.

*Primary Examiner* — Pancham Bakshi
(74) *Attorney, Agent, or Firm* — Betty J. Zea (57) ABSTRACT

A method of treating a skin condition including applying a rinse-off multi-phase cleansing composition including a cleansing phase including an anionic surfactant and zinc pyrithione and a benefit phase including a benefit agent.

18 Claims, 1 Drawing Sheet

(56) References Cited

U.S. PATENT DOCUMENTS

| | | |
|---|---|---|
| 8,105,996 B2 | 1/2012 | Wei et al. |
| 8,119,168 B2 | 2/2012 | Johnson et al. |
| 8,158,566 B2 | 4/2012 | Wei |
| 8,491,877 B2 | 7/2013 | Schwartz et al. |
| 9,675,530 B2 | 6/2017 | Focht et al. |
| 2003/0068289 A1 | 4/2003 | Bailey et al. |
| 2004/0161435 A1 | 8/2004 | Gupta |
| 2004/0191331 A1 | 9/2004 | Schwartz et al. |
| 2004/0213751 A1 | 10/2004 | Schwartz et al. |
| 2005/0118276 A1 | 6/2005 | Lei et al. |
| 2005/0244352 A1 | 11/2005 | Lemoine et al. |
| 2007/0009463 A1 | 1/2007 | Niebauer et al. |
| 2007/0128147 A1 | 6/2007 | Schwartz et al. |
| 2007/0190177 A1 | 8/2007 | Kling et al. |
| 2008/0063618 A1 | 3/2008 | Johnson et al. |
| 2008/0138442 A1 | 6/2008 | Johnson et al. |
| 2008/0160093 A1 | 7/2008 | Schwartz et al. |
| 2008/0206355 A1 | 8/2008 | Schwartz et al. |
| 2008/0249136 A1 | 10/2008 | Annis et al. |
| 2011/0039469 A1 | 2/2011 | Cabell et al. |
| 2011/0197906 A1 | 8/2011 | Schwartz |
| 2011/0197907 A1 | 8/2011 | Schwartz |
| 2011/0200649 A1 | 8/2011 | Schwartz |
| 2011/0200650 A1 | 8/2011 | Schwartz |
| 2011/0201588 A1 | 8/2011 | Schwartz |
| 2012/0009285 A1* | 1/2012 | Wei .................. A61K 8/0258 424/757 |
| 2012/0039966 A1 | 2/2012 | Capretta et al. |
| 2012/0103151 A1 | 5/2012 | Jones et al. |
| 2012/0216408 A1 | 8/2012 | Cook et al. |
| 2012/0219610 A1 | 8/2012 | Smith, III et al. |
| 2012/0220516 A1 | 8/2012 | Smith et al. |
| 2012/0246851 A1 | 10/2012 | Smith, III et al. |
| 2012/0324736 A1 | 12/2012 | Eagleton |
| 2013/0042482 A1 | 2/2013 | Bradford et al. |
| 2013/0045248 A1 | 2/2013 | Coffindaffer et al. |
| 2013/0045255 A1 | 2/2013 | Smith, III et al. |
| 2013/0045256 A1 | 2/2013 | Schwartz |
| 2013/0045257 A1 | 2/2013 | Alwattari et al. |
| 2013/0045263 A1 | 2/2013 | Smith, III et al. |
| 2013/0045284 A1 | 2/2013 | Stella |
| 2013/0045285 A1 | 2/2013 | Stella et al. |
| 2013/0045907 A1 | 2/2013 | Lanzalaco et al. |
| 2013/0045961 A1 | 2/2013 | Smith, III et al. |
| 2013/0048005 A1 | 2/2013 | Smith, III et al. |
| 2013/0205959 A1 | 8/2013 | Jones et al. |
| 2013/0222057 A1 | 8/2013 | Henshaw |
| 2013/0280200 A1 | 10/2013 | Schwartz |
| 2013/0303503 A1 | 11/2013 | Smith, III et al. |
| 2014/0274852 A1 | 9/2014 | Jiang et al. |
| 2014/0303135 A1 | 10/2014 | Smith, III et al. |

FOREIGN PATENT DOCUMENTS

| | | |
|---|---|---|
| EP | 0093541 A2 | 11/1983 |
| EP | 0158481 A2 | 10/1985 |
| EP | 0196824 A2 | 10/1986 |
| EP | 0217635 A2 | 4/1987 |
| EP | 0285388 A2 | 10/1988 |
| EP | 0468564 A2 | 1/1992 |
| FR | 2 685 638 A1 | 7/1993 |
| JP | 2006-176675 | 12/2004 |
| WO | 94/14408 A1 | 7/1994 |
| WO | 94/14409 A1 | 7/1994 |
| WO | 99/66886 A1 | 12/1999 |
| WO | 02/00178 A1 | 1/2002 |
| WO | 2006/110386 A1 | 10/2006 |
| WO | WO 2011/156672 A2 | 12/2011 |
| WO | WO 2014/205088 A2 | 12/2014 |

* cited by examiner

METHODS OF COSMETICALLY TREATING SKIN CONDITIONS WITH A COSMETIC PERSONAL CLEANSING COMPOSITION

TECHNICAL FIELD

The present disclosure generally relates to methods of treating skin conditions by applying a multi-phase cleansing composition comprising zinc pyrithione.

BACKGROUND

Skin conditions are often treated with leave on products, like ointments or creams. This is often an additional step to the sufferer's everyday routine. To help with compliance, it would be ideal to be able to treat skin conditions as part of a sufferer's everyday routine, like showering. As such, it is desirable to treat skin conditions with rinse off cleansing compositions.

SUMMARY

A method of cosmetically treating a skin condition, comprising applying to at least a portion of the skin with the condition of an individual a rinse-off multi-phase cleansing composition comprising a cleansing phase comprising an anionic surfactant and zinc pyrithione, and a benefit phase comprising a benefit agent.

A method of treating atopic dermatitis, comprising applying a multi-phase cleansing composition to at least a portion of skin of an individual with atopic dermatitis, wherein the composition comprises a structured cleansing phase comprising from about 3% to about 20%, by weight of the composition, of sodium trideceth(n) sulfate, wherein n is about 2.0, and from about 0.01% to about 5.0%, by weight of the composition, of zinc pyrithione; and from about 1% to about 30%, by weight of the composition, of a benefit phase, comprising from about 1% to about 3% by weight of the composition, of glyceryl monooleate and from about 5% to about 15%, by weight of the composition, of petrolatum.

These and other methods and compositions are described in more detail below.

DETAILED DESCRIPTION

I. Definitions

As used herein, the following terms shall have the meaning specified thereafter:

"Anhydrous" refers to those compositions, and components thereof, which are substantially free of water.

"Cleansing composition" refers to compositions intended for topical application to skin followed closely in time by rinsing with water. The cleaning compositions can be extrudable or dispensable from a package and can be in the form of, for example, a liquid, semi-liquid cream, lotion, gel, or a combination thereof.

"Multiphase" refers to compositions comprising at least two phases which can be chemically distinct (e.g. a cleansing phase and a benefit phase). Such phases can be in direct physical contact with one another. The phases can be blended or mixed to a significant degree, but still be physically distinct. In these situations, the physical distinctiveness is undetectable to the naked eye. The phases can also be in physical contact and visually distinct. Visually distinct phases can take many forms, for example, they can appear as stripes, marbled, etc. The composition can also be a combination of blended and visually distinct phases. The phases within a multiphase composition are generally stable meaning if the phases are visually separate upon filling they do not mix to a significant degree upon sitting in the package and if they are blended they do not phase separate upon sitting in the package, over the shelf life of the product.

"Package" refers to any suitable container for a cleansing composition including but not limited to a bottle, tottle, tube, jar, non-aerosol pump, and combinations thereof.

"Rinse-off" refers to compositions intended for topical usage in the presence of water either by hand or using an implement (towel, puff, sponge or other cleansing implements) and then rinsed away by water within seconds to minutes of application.

"Skin condition" refers to a condition on skin, excluding the scalp, which is associated with an infection. Skin with a skin condition can be referred to herein as diseased skin.

"STnS" refers to sodium trideceth(n) sulfate, wherein n can define the average number of moles of ethoxylate per molecule.

"Structured" refers to having a rheology that can confer stability on the cleansing composition. A degree of structure can be determined by characteristics determined by one or more of the following methods: Young's Modulus Method, Yield Stress Method, or Zero Shear Viscosity Method or by an Ultracentrifugation Method, described in U.S. Pat. No. 8,158,566, granted on Apr. 17, 2012. A cleansing phase can be considered to be structured if the cleansing phase has one or more following characteristics: (a) Zero Shear Viscosity of at least 100 Pascal-seconds (Pa-s), at least about 200 Pa-s, at least about 500 Pa-s, at least about 1,000 Pa-s, at least about 1,500 Pa-s, or at least about 2,000 Pa-s; (b) A Structured Domain Volume Ratio as measured by the Ultracentrifugation Method, of greater than about 40%, at least about 45%, at least about 50%, at least about 55%, at least about 60%, at least about 65%, at least about 70%, at least about 75%, at least about 80%, at least about 85%, or at least about 90%; or (c) A Young's Modulus of greater than about 2 Pascals (Pa), greater than about 10 Pa, greater than about 20 Pa, greater than about 30 Pa, greater than about 40 Pa, greater than about 50 Pa, greater than about 75 Pa, or greater than about 100 Pa.

The phrase "substantially free of" as used herein, unless otherwise specified means that the composition or method comprises less than about 3%, less than about 1%, or even less than about 0.1% of the stated ingredient. The term "free of" as used herein means that the composition or method comprises 0% of the stated ingredient, which is the ingredient has not been added to the composition. However, these ingredients may incidentally form as a byproduct or a reaction product of the other components of the cleansing composition.

II. Compositions and Methods for Treating Skin Conditions

Cleansing and barrier supplementation by, e.g., creams and lotions, especially containing exogenous lipids such as petrolatum, can be useful for cosmetic treatment of barrier compromised skin. However, while multiphase cleansing compositions can improve skin barrier properties by depositing a lipid, they are generally ineffective against microorganisms which have established a presence and/or are associated with a skin condition. Many skin conditions may be caused by or associated with microorganisms, which can be invasive species or even local, opportunistic species, which advantageously propagate under certain conditions on the skin like a skin wound. Further, many skin conditions can degenerate to a state that drug treatment by professionals can be required.

Actives are often used in the treatment of diseased skin. While it is suggested that zinc containing and/or pyrithione materials have some benefits on skin, these properties are usually attributed to leave on products, like lotion or creams. This is due, at least in part, to the ability to efficaciously deliver zinc containing and/or pyrithione materials from these leave-on forms. Delivering zinc and/or pyrithione materials to the skin from a rinse-off product is a challenge. There is limited residence time on the skin. Moreover, when the rinse-off composition is a cleanser, you are trying to simultaneously remove things from the skin (like dirt and excess sebum) and deposit things on the skin (like zinc pyrithione).

In addition, people with a skin condition often find cleansing can be irritating to the skin, and, when the skin barrier is severely compromised, cleansing products can further damage the skin. Thus, cleansing products designed for non-diseased skin, like dry skin, cannot necessarily be reapplied to diseased skin.

The present inventors have surprisingly discovered that rinse-off multiphase cleansing compositions comprising a zinc and/or pyrithione material and a benefit agent can be used to cosmetically treat a skin condition by, for example, improving the barrier properties of the skin and/or depositing actives on the skin. Without being limited by theory, it is believed such a composition can deposit lipid to facilitate skin barrier improvement, and an active agent, like zinc pyrithione having broad spectrum biocidal properties against a diverse range of microorganisms, in a sufficient dose to elicit a strong response (e.g. more than 1 log greater bacterial reduction than a placebo with no zinc pyrithione) against the target microorganisms. As can be seen in Table 1 below, an inventive multiphase cleansing composition with a benefit agent and with 0.5% zinc pyrithione, by weight of the composition, provided a log reduction versus a placebo (the inventive composition without zinc pyrithione) of 2.62 in growth of staph aureus. The inventive composition also provided a much enhanced benefit over comparative examples 1 and 2 which were cleansing compositions without a benefit agent but with zinc pyrithione. The ability to utilize a rinse-off multiphase cleansing composition for treatment could avoid the need for treatment with a drug, which often has adverse side effects.

TABLE 1

| Composition | Log reduction vs placebo | % Reduction vs. placebo |
| --- | --- | --- |
| Comparative 1, 150 ppm zinc pyrithione | 0.77 | 83.05 |
| Comparative 2, 0.2% zinc pyrithione | 0.94 | 86.06 |
| Inv. Composition, 0.5% zinc pyrithione | 2.62 | 99.40 |

Figure 1:
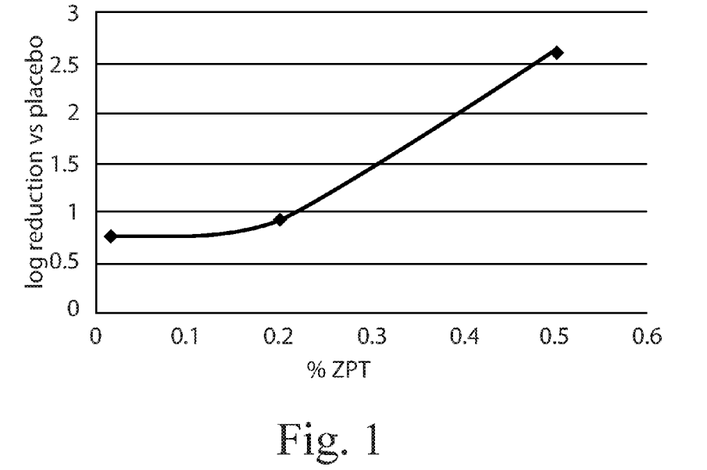
FIG. 1 is a graph of the log reduction of staph aureus versus the percent of zinc pyrithione in a multiphase cleansing composition.

Additionally, as can be seen in FIG. 1, a rinse-off multiphase cleansing composition comprising a benefit agent and at least about 0.25% zinc pyrithione, by weight of the composition, can provide an unexpected and disproportionate bacterial reduction in staph aureus. The log reduction effect is surprisingly not linear with the zinc pyrithione level. In fact, the effect appears to be synergist starting at about 0.25% zinc pyrithione, by weight of the composition, when the composition comprises a benefit agent. Without being limited by theory, it is believed the co-deposited benefit agent facilitates transport of the zinc pyrithione onto the skin surface enhancing the activity of the zinc pyrithione to yield the disproportionate effect. It is also possible the benefit agent enhances deposition of the zinc pyrithione such that the composition with the benefit agent deposits more zinc pyrithione than expected and results in enhanced efficacy. Either way, the impact to log reduction in a composition with both a benefit agent and zinc pyrithione is demonstrated.

Skin with a skin condition, like atopic dermatitis, can have a reduced ability to fight off bacteria. For example, skin with atopic dermatitis expresses less antimicrobial peptides. These peptides are involved in combating infection. Thus, zinc pyrithione, because of its breadth of activity against pathogens, is well suited to help combat skin infection associated with such skin conditions.

In addition to having a direct impact on log reduction of bacteria, it is also believed that zinc pyrithione can impact the pathogenesis of diseased skin. While the triggers of disorder in skin disease pathogenesis vary, the events associated with the elicitation of a lesion share many features in common. This strongly suggests the existence of genes/proteins that play fundamental roles in the establishment and maintenance of epidermal homeostasis.

Previously, a gene expression signature was identified that is present in a large number of inflammatory skin diseases (see WO 2014/028569). It has since been discovered that this signature is also a feature of more mild disturbances of epidermal homeostasis such as seasonal xerosis, and surfactant and mechanical damage to the stratum corneum. Accordingly, expression of this signature appears to be a near universal feature of disrupted skin (i.e. the Unhealthy Skin Signature).

Surprisingly, using pattern matching algorithms and a subset of the genes within the Unhealthy Skin Signature, it has been discovered that zinc pyrithione displays negative linkage to several instances of normal human keratinocytes treated with various doses of zinc pyrithione for times ranging from 6-24 hours. The scores strongly suggest the capacity of zinc pyrithione to effect a reversal of this important pattern of gene expression. Thus, delivery of zinc pyrithione to the skin of an individual with a skin condition could be beneficial in the treatment of the skin condition.

Furthermore, the present inventors also surprisingly discovered rinse-off multiphase cleansing compositions comprising a zinc and/or pyrithione material and a benefit agent can be used to treat skin conditions without irritating the already compromised skin. Surfactant containing compositions are inherently irritating to skin due to the interaction of surfactants with skin cells, enzymes, etc. The present compositions are mild to the skin, demonstrating reduced cytokine expression (a sign of reducing inflammation in the skin) and increased levels of natural moisturizing factors (a sign of increased moisture) in the skin exposed during clinical evaluation.

In fact, not only can there be less irritation to the barrier compromised skin, but a composition comprising a benefit agent and a zinc and/or pyrithione material can improve the skin barrier. Take a look at FIG. 2 and Table 2. Trans epidermal water loss (TEWL) measures the amount of moisture that passes from inside the body, through the skin, to the external environment (g/m² per hour). As the skin barrier property decreases, TEWL tends to increase, showing a corresponding loss of water through the skin. A composition (Inventive Example 1) with 15% by weight of a benefit agent (14.7% of petrolatum and 0.3% by weight of glyceryl monooleate) and 0.5% by weight of a zinc and/or pyrithione material (zinc pyrithione) showed an improvement in TEWL versus the study control (water only) after 21 days. Inventive Example 1 even outperformed Comparative Example A (the same benefit agent containing cleansing composition without the zinc pyrithione) and a marketed body wash for atopic dermatitis, Comparative B, after 21 days of use when measured 3 hours after cleansing. This infers the combination of lipid with zinc pyrithione delivers unexpected barrier improvement beyond the current body wash with lipid only.

TABLE 2

Figure 2:
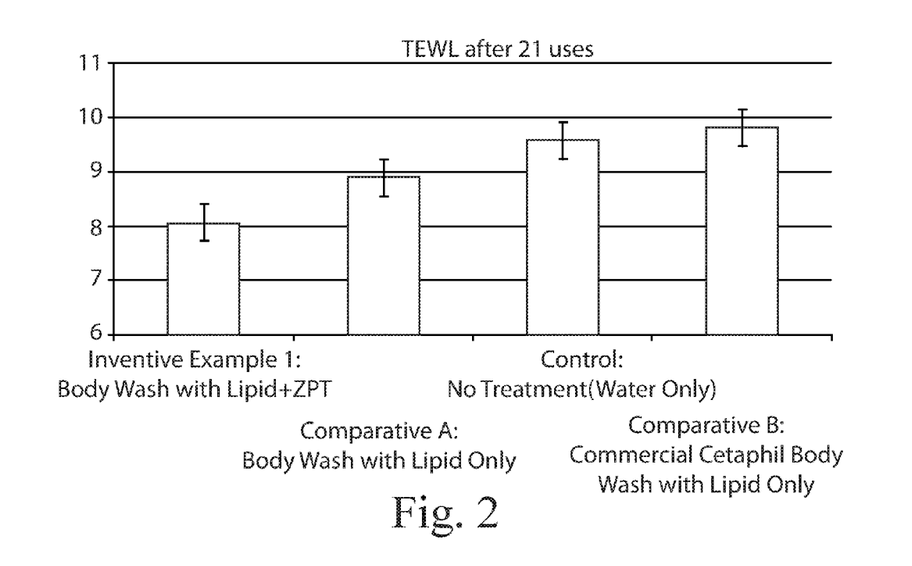
FIG. 2 is a graph showing the TEWL measurements (in $g/m^2$) of the noted compositions after 21 uses.

| | TEWL After 21 uses | Group* | p values vs. Control | Standard Error |
|---|---|---|---|---|
| Inventive Example 1: Body Wash with Lipid + ZPT | 8.065 | a | 0.0001 | 0.35 |
| Comparative A: Body Wash with Lipid Only | 8.905 | b | 0.0746 | 0.346 |
| Control: No Treatment (Water Only) | 9.58 | bc | — | 0.346 |
| Comparative B: Commercial Cetaphil Body Wash with Lipid Only | 9.803 | c | 0.5488 | 0.345 |

*Treatment with the same grouping letter(s) are not significantly different from each other at alpha = 0.05.

A. Rinse-Off Cleaning Compositions

Zinc and/or pyrithione materials can be applied to the skin through a rinse-off cleansing composition. Suitable zinc and pyrithione materials are discussed below. A rinse-off cleansing composition can include a cleansing phase and a benefit phase. The cleansing phase can include, for example, various surfactants as described herein. The cleaning phase and the benefit phase can be blended, and/or patterned.

The rinse-off cleansing composition may be free of sodium lauryl sulfate. The rinse-off cleansing composition may have at least a 70% lamellar structure.

i. Cleansing Phase

As noted herein, a cleansing phase can include at least one surfactant. The concentration of surfactant in the cleansing composition can range from about 1% to about 20%, by weight of the cleansing composition; from about 3% to about 20%, from about 2% to about 15%, by weight; and from about 5% to about 10%, by weight of the cleansing composition. The cleansing phase can include, for example, an aqueous structured surfactant phase.

Such a structured surfactant phase can include a structuring surfactant like sodium trideceth(n) sulfate, hereinafter STnS, wherein n can define average moles of ethoxylation. n can range from about 0 to about 3. n can also range from about 0.5 to about 2.7, from about 1.1 to about 2.5, from about 1.8 to about 2.2, or n can be about 2. When n can be less than 3, STnS can provide improved stability, improved compatibility of benefit agents within the rinse-off cleansing compositions, and increased mildness of the rinse-off cleansing compositions, such described benefits of STnS are disclosed in U.S. Patent Application Publication No. 2012/0009285.

The cleansing phase can comprise a non-structuring surfactant, like sodium lauryl sulfate and/or sodium laureth(n) sulfate, wherein n can define average moles of ethoxylation. n can range from about 1 to about 3. Suitable examples of sodium laureth(n) sulfate are described in U.S. Patent Application Publication No. 2010/0322878. Additionally, the cleansing composition can be free of sodium lauryl sulfate.

Further, the cleansing phase can comprise a structuring system, wherein the structuring system can comprise, a non-ionic emulsifier, from about 0.01% to about 5%, by weight of the rinse-off cleansing composition, of an associative polymer; an electrolyte, or combinations thereof.

Nonionic emulsifiers suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include tridecyl alcohol ethoxylate-3 (TDA-3), cocoamide monoethanolamine, decyl glucoside, or a combination thereof. Additional suitable emulsifiers are described in U.S. Patent Application Publication No. 2012/0009285. A cleansing phase may include, for example, from about 0.1% to about 5%, from about 0.5% to about 2.5%, or from about 0.75% to about 2%, by weight of the composition, of a nonionic emulsifier.

The rinse-off cleansing composition can further comprise from about 0.1% to 20%, by weight of the rinse-off cleansing composition, of a cosurfactant. Cosurfactants can comprise amphoteric surfactants, zwitterionic surfactants, or mixtures thereof. The rinse-off cleansing composition can include at least one of an amphoteric surfactant and a zwitterionic surfactant. Suitable amphoteric or zwitterionic surfactants can include those described in U.S. Pat. No. 5,104,646 and U.S. Pat. No. 5,106,609.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

A cleansing phase may comprise a zinc and/or pyrithione material. Examples of such zinc-containing materials can include, for example, zinc salts and zinc containing layered materials. A rinse-off cleansing composition can comprise at least about 0.01%, by weight of the rinse-off cleansing composition, of a zinc and/or pyrithione material. The rinse-off cleansing composition can also comprise from about 0.1% to about 5.0%, from about 0.2% to about 1.0%, from about 0.3% to about 0.6%, by weight of the rinse-off cleansing composition, of a zinc and/or pyrithione material. The rinse-off cleansing composition can also comprise about 0.5%, by weight of the rinse-off cleansing composition, of zinc pyrithione.

Examples of zinc salts useful herein can include the following: zinc aluminate, zinc carbonate, zinc oxide, zinc phosphates, zinc selenide, zinc sulfide, zinc silicates, zinc silicofluoride, zinc borate, zinc hydroxide, zinc hydroxy sulfate, zinc pyrithione, and combinations thereof.

One zinc salt, zinc pyrithione, is also known as a mercaptopyridine-N-oxide zinc salt. The zinc pyrithione can be made, for example, by reacting 1-hydroxy-2-pyridinethione (i.e., pyrithione acid) or a soluble salt thereof with a zinc salt (e.g. zinc sulfate) to form a zinc pyrithione precipitate as illustrated in U.S. Pat. No. 2,809,971 and the zinc pyrithione can be formed or processed into platelet zinc pyrithione using, for example, sonic energy as illustrated in U.S. Pat. No. 6,682,724.

Zinc pyrithione can take the form of particulates, platelets, or a combination thereof. For example, where the zinc pyrithione is introduced as particulate, such particulates may have an average particle size from about 0.1 µm to about 20 µm; such particulates may also have an average particle size from about 0.2 µm to about 10 µm. Particulate zinc pyrithione may have an average particle of about 5 µm or less, or even less than about 3 µm. Platelets may have an average diameter of about 2.5 µm and a thickness of less than about 1 µm. Smaller zinc pyrithione particles, having an average diameter of less than about 2 microns, can provide an increased surface area and speed of dissolution on the skin.

Examples of zinc-containing layered materials useful herein can include zinc-containing layered structures with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials may have zinc incorporated in the layers and/or be components of the gallery ions. Many zinc-containing layered materials occur naturally as minerals. Common examples include hydrozincite (zinc carbonate hydroxide), basic zinc carbonate, aurichalcite (zinc copper carbonate hydroxide), rosasite (copper zinc carbonate hydroxide), and combinations thereof. Natural zinc-containing layered materials can also occur where anionic layer species such as clay-type minerals (e.g., phyllosilicates) contain ion-exchanged zinc gallery ions. All of these natural materials can also be obtained synthetically or formed in situ in a composition or during a production process.

Another common class of zinc-containing layered materials, which are often, but not always, synthetic, is layered doubly hydroxides, which are generally represented by the formula $[M^{2+}_{1-x}M^{3+}_x(OH)_2]^{x+} A^{m-}_{x/m} \cdot nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of zinc-containing layered materials can be prepared and is called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1+x}(OH)_{3(1-y)}]^+$ $A^{n-}_{(1=3y)/n} \cdot nH_2O$ where the two metal ions may be different; if they are the same and represented by zinc, the formula simplifies to $[Zn_{1+x}(OH)_2]^{2x+2x} A^- \cdot nH_2O$. This latter formula represents (where x=0.4) and contains common materials such as zinc hydroxychloride and zinc hydroxynitrate. These are related to hydrozincite as well wherein a divalent anion replaces the monovalent anion. These materials can also be formed in situ in a composition or in or during a production process. These classes of zinc-containing layered materials represent relatively common examples of the general category and are not intended to be limiting as to the broader scope of materials which fit this definition.

Carbonates, especially zinc carbonate, may be useful as zinc materials or in combination with zinc pyrithione, which may enhance the activity of zinc pyrithione against microorganisms. Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Suitable examples of pyrithione materials can include zinc pyrithione, sodium pyrithione, pyrithione acid, dipyrithione, chitosan pyrithione, magnesium disulfide pyrithione, copper pyrithione, and combinations thereof. Pyrithione materials may also include other pyridinethione salts formed from heavy metals such as zinc, tin, cadmium, magnesium, aluminum, and zirconium.

A cleansing phase of a rinse-off cleansing composition can also include an associative polymer. Such associative polymer can be a crosslinked, alkali swellable, associative polymer comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in a presence of an electrolyte.

The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis, or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains. The acidic monomer can comprise any acid functional group, for example sulfate, sulfonate, carboxylate, phosphonate, or phosphate or mixtures of acid groups. The acidic monomer can comprise a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be an alkyl ester, an alkyl (meth)acrylate, where (meth)acrylate is understood to mean either methyl acrylate or acrylate, or mixtures of the two.

The hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the lathering, structured surfactant composition at low levels of polymer structurant.

The associative polymer can be Aqupec SER-300 made by Sumitomo Seika of Japan, which is Acrylates/C10-30 alkyl acrylate crosspolymer and comprises stearyl side chains with less than about 1% HM. Other associative polymers can comprise stearyl, octyl, decyl and lauryl side chains. Associative polymers can be Aqupec SER-150 (acrylates/C10-30 alkyl acrylates crosspolymer) comprising about C18 (stearyl) side chains and about 0.4% HM, and Aqupec HV-701EDR which comprises about C8 (octyl) side chains and about 3.5% HM. The associative polymer can be Stabylen 30 manufactured by 3V Sigma S.p.A., which has branched isodecanoate hydrophobic associative side chains.

A rinse-off cleansing composition can additionally comprise an organic cationic deposition polymer. A composition may comprise from about 0.01% to about 1.0%, from about 0.2% to about 0.8%, from about 0.3% to about 0.5%, by weight of the composition, of a cationic deposition polymer. Suitable cationic deposition polymers for use in the compositions of the present invention contain cationic nitrogen-containing moieties such as quaternary ammonium moieties. Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

The deposition polymers of the present invention can have a cationic charge density from about 0.8 meq/g to about 2.0 meq/g, alternatively from about 1.0 meq/g to about 1.5 meq/g.

ii. Benefit Phase

As noted herein, rinse-off cleansing compositions can include a benefit phase. The benefit phase can be hydrophobic and/or anhydrous. The benefit phase can also be substantially free of or free of, surfactant. The cleansing composition can comprise from about 1% to about 30%, by weight of the composition, or from about 8% to about 20%, by weight of the composition, of a benefit phase.

The benefit phase can also include a benefit agent. In particular, the benefit phase can comprise from about 0.1% to about 50%, by weight of the rinse-off cleansing composition, of the benefit agent. The benefit phase can also include from about 0.5% to about 20%, by weight of the rinse-off cleansing composition, of the benefit agent. Examples of the benefit agent can include artificial sweat, castor oil, olive oil, oleic acid, Sefose® 1618S, Sefose® 1618U, petrolatum, glyceryl monooleate, mineral oil, natural oils (e.g., soybean oil), and mixtures thereof. For example, a composition can include from about 1% to about 3%, by weight of the composition, of monoglyceryl monooleate and from about 5% to about 15%, by weight of the composition, of petrolatum. Other suitable benefit agents are described in U.S. Patent Application Publication No. 2012/0009285.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, soybean oil, vegetable oils, sunflower seed oil, vegetable oil derivatives, coconut oil and derivatized coconut oil, cottonseed oil and derivatized cottonseed oil, jojoba oil, cocoa butter, petrolatum, mineral oil, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein can include oleyl myristate, oleyl stearate, oleyl oleate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic skin benefit agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic skin benefit agents herein can include dimethicone copolyol, dimethylpolysiloxane, diethylpolysiloxane, mixed C1-C30 alkyl polysiloxanes, phenyl dimethicone, dimethiconol, and combinations thereof. Nonlimiting examples of silicone oils useful herein are described in U.S. Pat. No. 5,011,681. Still other suitable hydrophobic skin benefit agents can include milk triglycerides (e.g., hydroxylated milk glyceride) and polyol fatty acid polyesters.

A benefit phase may comprise a zinc and/or pyrithione material. Examples of such zinc-containing materials can include, for example, zinc salts and zinc containing layered materials. A rinse-off cleansing composition can comprise at least about 0.01%, by weight of the rinse-off cleansing composition, of a zinc and/or pyrithione material. The rinse-off cleansing composition can also comprise from about 0.1% to about 5.0%, from about 0.2% to about 1.0%, from about 0.3% to about 0.6%, by weight of the rinse-off cleansing composition, of a zinc and/or pyrithione material. The rinse-off cleansing composition can also comprise about 0.5%, by weight of the rinse-off cleansing composition, of zinc pyrithione.

Examples of zinc salts useful herein can include the following: zinc aluminate, zinc carbonate, zinc oxide, zinc phosphates, zinc selenide, zinc sulfide, zinc silicates, zinc silicofluoride, zinc borate, zinc hydroxide, zinc hydroxy sulfate, zinc pyrithione, and combinations thereof.

One zinc salt, zinc pyrithione, is also known as a mercaptopyridine-N-oxide zinc salt. The zinc pyrithione can be made, for example, by reacting 1-hydroxy-2-pyridinethione (i.e., pyrithione acid) or a soluble salt thereof with a zinc salt (e.g. zinc sulfate) to form a zinc pyrithione precipitate as illustrated in U.S. Pat. No. 2,809,971 and the zinc pyrithione can be formed or processed into platelet zinc pyrithione using, for example, sonic energy as illustrated in U.S. Pat. No. 6,682,724.

Zinc pyrithione can take the form of particulates, platelets, or a combination thereof. For example, where the zinc pyrithione is introduced as particulate, such particulates may have an average particle size from about 0.1 µm to about 20 µm; such particulates may also have an average particle size from about 0.2 µm to about 10 µm. Particulate zinc pyrithione may have an average particle of about 5 µm or less, or even less than about 3 µm. Platelets may have an average diameter of about 2.5 µm and a thickness of less than about 1 µm. Smaller zinc pyrithione particles, having an average diameter of less than about 2 microns, can provide an increased surface area and speed of dissolution on the skin.

Examples of zinc-containing layered materials useful herein can include zinc-containing layered structures with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials may have zinc incorporated in the layers and/or be components of the gallery ions. Many zinc-containing layered materials occur naturally as minerals. Common examples include hydrozincite (zinc carbonate hydroxide), basic zinc carbonate, aurichalcite (zinc copper carbonate hydroxide), rosasite (copper zinc carbonate hydroxide), and combinations thereof. Natural zinc-containing layered materials can also occur where anionic layer species such as clay-type minerals (e.g., phyllosilicates) contain ion-exchanged zinc gallery ions. All of these natural materials can also be obtained synthetically or formed in situ in a composition or during a production process.

Another common class of zinc-containing layered materials, which are often, but not always, synthetic is layered doubly hydroxides, which are generally represented by the formula $[M^{2+}_{1-x}M^{3+}_{x}(OH)_2]^{x+} A^{m-}_{x/m}.nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of zinc-containing layered materials can be prepared and is called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1+x}(OH)_{3(1-y)}]^+ A^{n-}_{(1=3y)/n}.nH_2O$ where the two metal ions may be different; if they are the same and represented by zinc, the formula simplifies to $[Zn_{1+x}(OH)_2]^{2x+}2x$ $A^-.nH_2O$. This latter formula represents (where x=0.4) and contains common materials such as zinc hydroxychloride and zinc hydroxynitrate. These are related to hydrozincite as well wherein a divalent anion replaces the monovalent anion. These materials can also be formed in situ in a composition or in or during a production process. These classes of zinc-containing layered materials represent relatively common examples of the general category and are not intended to be limiting as to the broader scope of materials which fit this definition.

Carbonates, especially zinc carbonate, may be useful as zinc materials or in combination with zinc pyrithione, which may enhance the activity of zinc pyrithione against microorganisms. Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Suitable examples of pyrithione materials can include zinc pyrithione, sodium pyrithione, pyrithione acid, dipyrithione, chitosan pyrithione, magnesium disulfide pyrithione, copper pyrithione, and combinations thereof. Pyrithione materials may also include other pyridinethione salts formed from heavy metals such as zinc, tin, cadmium, magnesium, aluminum, and zirconium.

Additional optional ingredients can also be added to the rinse-off cleansing composition for treatment of the skin, or to modify the aesthetics of the rinse-off cleansing composition as is the case with perfumes, colorants, dyes or the like. Optional materials useful in products herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit an ingredient to particularly stated application or applications listed. A precise nature of these optional materials, and levels of incorporation thereof, will depend on the physical form of the composition and the nature of the cleansing operation for which it is to be used. Optional materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less of the rinse-off cleansing composition.

To further improve stability under stressful conditions such as high temperature and vibration, densities of separate phases can be adjusted such that they can be substantially equal. To achieve this, low density microspheres can be added to one or more phases of the rinse-off cleansing composition. Examples of rinse-off cleansing compositions that comprise low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

The cleansing compositions may be useful as a component of a regimen. The regimen may include, in addition to the cleansing component, a leave on treatment, especially a leave on lotion comprising a lipid to improve the skin barrier. The leave on treatment may also include zinc containing materials, especially zinc oxide, zinc carbonate, zinc pyrithione, or a combination thereof.

B. Applying and Depositing Zinc and/or Pyrithione Materials

To cosmetically treat skin conditions, a zinc and/or pyrithione material can be applied to the skin from a rinse-off cleansing composition. The rinse-off cleansing composition can be multi-phase and comprise a cleansing phase and a benefit phase, wherein the benefit phase comprises a benefit agent. The skin condition being treated can include, for example, atopic dermatitis.

Additional skin conditions can include, for example, folliculitis, furunculosis (boils), abscesses, impetigo (school sores), methicillin resistant *Staphylococcus aureus*, staphylococcal scalded skin syndrome, toxic shock syndrome, tropical pyomyositis, botryomycosis (pyoderma vegetans), cellulitis, erysipelas, necrotizing fasciitis, infectious gangrene, scarlet fever, rheumatic fever, erythema marginatum, erythrasma, pitted keratolysis, trichomycosis axillaris, gonorrhea, meningococcal disease, erysipeloid, chancroid, urticarial, rosacea, rhinoscleroma, pneumonia, erythema, bullous eruptions, urticarial rashes, erythema multiforme, mucositis, wound infections, athlete's foot, gram negative folliculitis, chronic paronychia (green nail syndrome), spa pool folliculitis, ecthyma gangrenosum, granuloma inguinale, anthrax, gas gangrene, syphilis, yaws, pinta, cat scratch fever, bacillary angiomatosis, bartonellosis, tuberculosis, leprosy, atypical mycobacterial infections, leptospirosis, nocardiosis, bubonic plague, melioidosis, glanders, actinomycosis, septic shock, brucellosis, typhoid fever, lyme disease, relapsing fever, tularemia, rickettsial disease, ehrlichiosis, anaplasmosis, kawasaki disease, pseudofolliculitis barbae (shaving bumps), sarcoidosis, osier nodes, Janeway lesions (bacterial endocarditis), vaginitis, bacterial vaginosis, pyoderma, mycoses, furunculosis, eczema, seborrheic dermatitis, psoriasis, yeast infections, erysipelas, erhthrasma, hidradenitis suppurativa, lymphadenitis, lymphangitis, lymphedema, ringworm, tinea cruris, tinea corporis, tinea pedis, tinea capitis, tinea versicolor (pityriasis), candidiasis, intertrigo, thrush, sprotrichosis, phaeohyphomycosis, chromoblastomycosis, lobomycosis, sporotrichosis, shingles, warts, herpes simplex, or combinations thereof.

The method may further comprise rinsing the composition from the skin. The benefit agent may comprise petrolatum, monoglyceryl monooleate, or a combination thereof. In addition, where the benefit agent comprises a combination of petrolatum and glyceryl monooleate and the ratio of petrolatum to glyceryl monooleate is about 98:2, by weight of the benefit phase. The composition may be applied at least once per day for 5 or more days, 14 or more days, or even for 21 or more days. The composition may comprise from about 0.01% to about 5%, from about 0.25% to about 5.0%, from about 0.25% to about 1.0%, from about 0.3% to about 0.6%, or about 0.5%, by weight of the composition, of the zinc and/or pyrithione material. The anionic surfactant can comprise sodium trideceth(n) sulfate, wherein n is from about 0.5 to about 2.7, or n is about 2.0. In addition, the composition may further comprise from about 0.1% to about 5%, from about 0.5% to about 2.5%, or from about 0.75% to about 2%, by weight of the composition, of a nonionic emulsifier. The cleansing phase may further comprise from about 0.01% to about 1.0%, from about 0.2% to about 0.8%, or from about 0.3% to about 0.5%, by weight of the composition, of a cationic deposition polymer. The cationic deposition polymer can comprise, for example, hydroxypropyltrimonium chloride. The cationic deposition polymer can comprise a cationic charge density from about 0.8 meq/g to about 2.0 meq/g, or from about 1.0 meq/g to about 1.5 meq/g.

An exemplary method can include treating atopic dermatitis, comprising applying a multi-phase cleansing composition to at least a portion of skin of an individual with atopic dermatitis, wherein the composition comprises a structured cleansing phase comprising from about 3% to about 20%, by weight of the composition, of sodium trideceth(n) sulfate, wherein n is about 2.0, and from about 0.01% to about 5.0%, by weight of the composition, of zinc pyrithione; and from about 1% to about 30%, by weight of the composition, of a benefit phase, comprising from about 1% to about 3% by weight of the composition, of glyceryl monooleate and from about 5% to about 15%, by weight of the composition, of petrolatum. The composition may comprise from about 0.01% to about 5%, from about 0.2% to about 1.0%, from about 0.3% to about 0.6%, or about 0.5%, by weight of the composition, of the zinc pyrithione material. The anionic surfactant can comprise sodium trideceth(n) sulfate, wherein n is from about 0.5 to about 2.7, or n is about 2.0. In addition, the composition may further comprise from about 0.1% to about 5%, from about 0.5% to about 2.5%, or from about 0.75% to about 2%, by weight of the composition, of a nonionic emulsifier. The cleansing phase may further comprise from about 0.01% to about 1.0%, from about 0.2% to about 0.8%, or from about 0.3% to about 0.5%, by weight of the composition, of a cationic deposition polymer. The cationic deposition polymer can comprise, for example, hydroxypropyltrimonium chloride. The cationic deposition polymer can comprise a cationic charge density from about 0.8 meq/g to about 2.0 meq/g, or from about 1.0 meq/g to about 1.5 meq/g.

For the sake of brevity, all of the compositional elements and parameters noted above are not repeated herein, but can be used within the methods where relevant.

III. Procedures

A. Dry Skin Grade Screen and Application of Materials for Corneometer and Trans Epidermal Water Loss Testing The standard leg-controlled application protocol (LCAT) can be used to evaluate clinical performance of the compositions. Test subjects are screened for dry skin grade of 2.5-4.0 by trained expert graders following guidelines below. Visual evaluations will be done with the aid of an Illuminated Magnifying Lamp which provides 2.75× magnification and which has a shadow-free circular fluorescent light source (General Electric Cool White, 22 watt 8" Circline). At least 30 subjects are needed to obtain sufficient replicates for each treatment. Table 3 shows a grading scale for dry skin and lists the redness and dryness characteristics associated with each grade.

TABLE 3

| Grade* | Redness | Dryness** |
|---|---|---|
| 0.0 | No redness | Perfect skin |
| 1.0 | Barely detectable redness | Patches of checking and/or slight powderiness, occasional patches of small scales may be seen, distribution generalized |
| 2.0 | Slight redness | Generalized slight powderiness, early cracking, or occasional small lifting scales may be present |
| 3.0 | Moderate redness | Generalized moderate powderiness and/or heavy cracking and lifting scales |
| 4.0 | Heavy or substantial redness | Generalized heavy powderiness and/or heavy cracking and lifting scales |
| 5.0 | Severe redness | Generalized high cracking and lifting scales, eczematous change may be present, but not prominent, may see bleeding cracks |
| 6.0 | Extreme redness | Generalized severe cracking, bleeding cracks and eczematous changes may be present, large scales may be sloughing off |

*Half-unit grades may be used if necessary
**"Generalized" refers to situations where more than 50% of an application area is affected Before initial visual grading, a clinical assistant will mark 2-7 cm (across)×10 cm (down) treatment sites on an outer portion of the lower legs using a template and a laboratory marking pen (4 corner brackets are sufficient to delineate each area). For assignment of the products, two sites located on the left leg will be numbered L1 and L2, where L1 is the top part of the lower leg nearest the knee, and L2 is the bottom part of the lower leg nearest the ankle. Two sites located on the right leg will be numbered R1 and R2, where R1 is the top part of the lower leg nearest the knee, and R2 is the bottom part of the lower leg nearest the ankle.

To simplify the treatment process, master trays will be prepared for each treatment plan specified in the study randomization. Each master tray will be divided in half, with each half labeled 'left' or 'right' to indicate which leg it corresponds to, then subdivided into sections for the test products in the order of leg application site. One or more make-up trays can also be prepared for use as needed using individual coded containers, or other appropriate product code indicators, that can be re-arranged according to a given treatment plan.

Trained clinical assistants will wash each subject's lower legs in a controlled manner with assigned treatments once daily for 21 consecutive days. Assignment of test treatments to skin sites on the left and right legs will be designated by study randomization. A target dose of body wash for each site is 10 µL/cm². All body wash products will be dispensed at 0.7 mL dosages. All body wash test products will be drawn up into syringes at the 0.7 mL dosage. A one day supply of syringes for all products may be filled the day before or the day of use. Product that has been transferred to another container and the container itself will be used for one day only (i.e., the day the transfer occurred). All syringe filling operations will be appropriately documented (e.g., product code filled, when filled, initials of person responsible for filling).

The treatment area on the top part of the left leg of the subject is wetted for 5 seconds with 95-100° F. running tap water. The water flow rate is about 1200 mL per minute. For the "No Treatment" site, apply water only. For a treatment site, dispense 0.7 mL of body wash product from the syringe onto the center of the treatment area and place a wet puff over the dispensed product and gently rub the puff back and forth within the treatment site for 10 seconds. Then, allow lather (or water only) to remain on the site for 90 seconds. When residence time for a site has expired, the site is rinsed for 15 seconds under a running tap, taking care not to rinse adjacent sites. After the application area has been rinsed, the area is gently patted dry. Repeat the procedure for the lower part of the left leg, and after completion, use the same procedure for each of the top part of the right leg and the lower part of the right leg.

B. Corneometer Testing

Once the materials are applied as noted above in Section A, improvements in skin hydration can be measured with a Corneometer, while baseline measurements are taken prior to application of materials. In particular, skin hydration based upon measurements of capacitance can be assessed using the Corneometer® 825 as set forth in U.S. patent application Ser. No. 13/007,630. Such measurements can be non-invasive and can be taken in duplicate on each site of the subjects' legs at the following times: at baseline, prior to $1^{st}$ treatment; 3 hours post $1^{st}$, $3^{rd}$, $5^{th}$, $14^{th}$ and $21^{st}$ treatments; 24 hours post $4^{th}$, $13^{th}$ and $21^{st}$ treatments; 48 hours post $21^{st}$ treatment after a visual assessment has been completed. Subjects can be acclimated for a minimum of thirty minutes in an environmentally controlled room (maintained at 70° F.±2 and 30-45% relative humidity) prior to the non-invasive instrumental measurements taken on their legs. Data can be recorded electronically using a Sponsor's direct data entry and data capture programs. Measurements can be performed according to a test facility's standard operating procedures and/or the Sponsors Instrument Operation Manual.

The Corneometer values are arbitrary units for electrical impedance. At baseline, for subjects having a dry skin grade from about 2.5 to about 4.0, an adjusted mean of such Corneometer values can typically fall within a range of about 15 to about 20. Higher Corneometer values can correspond to a higher hydration level, and thus, lower Corneometer values can correspond to lower hydration levels.

The instrument should only be operated by trained operators. Further, the same instrument(s) and operator(s) can be used throughout the study. Kimwipes can be used to wipe an end of a probe. The probe can be wiped with a Kimwipe between each measurement. At the end of an evaluation session, data collected for that period can be backed up according to instructions in the Sponsors Instrument Operation Manual, and a hard copy of the data can be printed.

C. Trans Epidermal Water Loss Testing

Once the materials are applied as noted above in Section A, the integrity of the stratum corneum can be assessed by trans epidermal water loss (TEWL) using the Aquaflux® instrument. A single non-invasive measurement can be obtained on each of the lower leg treatment areas. The data can be captured electronically using the AquaFlux® system. The instrument should only be operated by trained operators. Further, the same instrument(s) and operator(s) can be used throughout the study. Kimwipes can be used to wipe the end of a probe. The probe should be wiped with a Kimwipe between each measurement.

IV. Examples

| Component | Inventive Example 1 | Inventive Example 2 | Inventive Example 3 | Inventive Example 4 | Comparative Example A |
|---|---|---|---|---|---|
| Sodium Trideceth-2 Sulfate | 8.21% | 8.73% | 9.24% | 8.73% | 8.21% |
| Cocoamidopropyl betaine | 2.45% | 2.61% | 2.76% | 2.61% | 2.45% |
| Sodium Chloride | 4.03% | 4.26% | 4.5% | 4.26% | 4.03% |
| Trideceth-3 | 1.31% | 1.39% | 1.48% | 1.39% | 1.31% |
| Guar hydroxypropyltrimonium chloride | 0.43% | 0.45% | 0.48% | 0.45% | 0.43% |
| Xanthan Gum | 0.19% | 0.21% | 0.22% | 0.21% | 0.19% |
| Acrylate/C10-C30 Alkyl Acrylates Crosspolymer | 0.03% | 0.03% | 0.03% | 0.03% | 0.03% |
| Sodium Benzoate | 0.27% | 0.29% | 0.30% | 0.29% | — |
| Citric Acid (50% in DI water) | To pH = 5.7 | To pH = 5.7 | To pH = 5.7 | To pH = 5.7 | To pH = 5.7 |
| Preservative | 0.04% | 0.04% | 0.04% | 0.04% | 0.04% |
| Perfume | 0.25% | 0.25% | 0.25% | 0.25% | 0.25% |
| Zinc Pyrithione (FPS grade) | 0.5% | 0.3% | 0.1% | 0.3% | — |
| Water and Minors | Q.S. | Q.S. | Q.S. | Q.S. | Q.S. |
| Petrolatum | 14.70% | 9.80% | 4.90% | — | 14.70% |
| Glyceryl monooleate | 0.30% | 0.20% | 0.10% | 0.10% | 0.30% |
| Soybean Oil | — | — | — | 9.90% | — |
| Butylated Hydroxytoluene (BHT) | — | — | — | 0.20% | — |

The exemplary cleansing compositions can be prepared by the following procedure. First, prepare the aqueous phase of the composition by adding water to a mixing vessel. Add sodium chloride to the vessel and wait until it fully dissolves. Add sodium trideceth sulfate to the mixing vessel. Add the following the ingredients to the main mixing vessel with adequate mixing: guar hydroxypropyltrimonium chloride and xanthan gum. Then, prepare a premix of trideceth-3 with Acrylate/C10-C30 Alkyl Acrylates crosspolymer and add the premix into the main mixing vessel. Then, add cocoamidopropyl betaine followed by sodium benzoate. Adjust the pH of the composition to about 5.7 using citric acid solution. Then, add perfume and Kathon CG preservative, zinc pyrithione (where included), and other minor ingredients. Keep mixing until the composition is uniform.

For Inventive Compositions 1-3 and Comparative Composition A, prepare the lipid phase of the compositions in a separate vessel by first adding petrolatum (when included) or and heat the vessel to about 90° C. Then, add glyceryl monooleate with mixing. Cool the lipid phase to about 55° C. Then, add the lipid phase into the cleansing phase under controlled shear conditions, such that the lipid particles are larger than about 50 microns. For Inventive Example 4, prepare the lipid phase in a separate vessel by first adding soybean oil and heat the vessel to about 45° C. Then add glyceryl monooleate and butylated hydroxytoluene with good mixing. Then, add the lipid phase into the cleansing phase under controlled shear conditions, such that the lipid particles are about 1-5 microns.

The comparative B, noted above, is a commercial Cetaphil Eczema Calming Body Wash. The full ingredients of the Cetaphil Body Wash are: Water, Butyrospermum Parkii (Shea Butter), Sodium Trideceth Sulfate, Glycerin, Helianthus Annuus (Sunflower) Seed Oil, Sodium Chloride, Sodium Lauroamphoacetate, Cocamide MEA, Niacinamide, Tocopheryl Acetate, Allantoin, Arginine, Citric Acid, Methylisothiazolinone, Sodium PCA, 1, 2 Hexanediol, Caprylyl Glycol, Guar Hydroxypropyltrimonium Chloride, Potassium Sorbate, Disodium EDTA.

Exemplary Combinations

A. A multiphase cleansing composition, comprising a cleansing phase comprising an anionic surfactant and a benefit phase comprising a benefit agent and zinc pyrithione.

B. The composition of paragraph A, wherein the composition comprises from about 1% to about 20%, from about 3% to about 20%, from about 2% to about 15%, or from about 5% to about 10%, by weight of the cleansing composition, of surfactant.

C. The composition of paragraphs A or B, wherein the anionic surfactant comprises sodium trideceth(n) sulfate, wherein n can range from about 0 to about 3, from about 0.5 to about 2.7, from about 1.1 to about 2.5, from about 1.8 to about 2.2, or n can be about 2.

D. The composition of paragraphs A-C, wherein the composition further comprises from about 0.1% to about 5%, from about 0.5% to about 2.5%, or from about 0.75% to about 2%, by weight of the composition, of a nonionic emulsifier.

E. The composition of paragraphs A-D, further comprising from about 0.1% to 20%, by weight of the rinse-off cleansing composition, of a cosurfactant, wherein the cosurfactant comprises an amphoteric surfactant, a zwitterionic surfactant, or a combination thereof.

F. The composition of paragraph E, wherein the cosurfactant comprises cocoamidopropyl betaine.

G. The composition of paragraphs A-F, further comprising an associative polymer.

H. The composition of paragraph G, wherein the associative polymer comprises an acrylates/C10-30 alkyl acrylate crosspolymer.

I. The composition of paragraphs A-H, further comprising from about 0.01% to about 1.0%, from about 0.2% to about 0.8%, or from about 0.3% to about 0.5%, by weight of the composition, of a cationic deposition polymer.

J. The composition of paragraph I, wherein the cationic deposition polymer comprises guar hydroxypropyltrimonium chloride.

K. The composition of paragraphs I or J, wherein the cationic deposition polymer has a cationic charge density from about 0.8 meq/g to about 2.0 meq/g, or from about 1.0 meq/g to about 1.5 meq/g.
L. The composition of paragraphs A-K, wherein the benefit phase is substantially free of surfactant.
M. The composition of paragraphs A-L, wherein the composition comprises from about 1% to about 30%, or from about 8% to about 20%, by weight of the composition, of the benefit phase.
N. The composition of paragraphs A-M, wherein the composition comprises from about 0.1% to about 50%, by weight of the rinse-off cleansing composition, of the benefit agent.
O. The composition of paragraphs A-M, wherein the benefit phase comprises from about 0.5% to about 20%, by weight of the rinse-off cleansing composition, of the benefit agent.
P. The composition of paragraphs A-O, wherein the benefit agent comprises castor oil, olive oil, oleic acid, sucrose polyester, petrolatum, monoglyceryl monooleate, mineral oil, soybean oil, or a combination thereof.
Q. The composition of paragraphs A-O, wherein the benefit agent comprises a petrolatum and monoglyceryl monooleate.
R. The composition of paragraph Q, wherein the composition comprises from about 1% to about 3%, by weight of the composition, of the monoglyceryl monooleate and from about 5% to about 15%, by weight of the composition, of the petrolatum.
S. The composition of paragraphs A-R, wherein the composition comprises from about 0.01% to about 5%, from about 0.25% to about 5.0%, from about 0.25% to about 1.0%, from about 0.3% to about 0.6%, or about 0.5%, by weight of the composition, of the zinc pyrithione.
T. Use of a multiphase cleansing composition as defined in any of paragraphs A-S, for improving the barrier property of skin.
U. A multiphase cleansing composition as defined in any of paragraphs A-S, for treating a skin condition.
V. A multiphase cleansing composition as defined in any of paragraphs A-S, for treating a skin condition.
W. A multiphase cleansing composition as defined in any of paragraphs A-S, for treating atopic dermatitis.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating atopic dermatitis, comprising applying to at least a portion of the skin of an individual with atopic dermatitis a rinse-off multi-phase cleansing composition comprising a cleansing phase comprising an anionic surfactant and zinc pyrithione and a benefit phase comprising a benefit agent.

2. The method of claim 1, further comprising rinsing the multi-phase cleansing composition from the skin of the individual.

3. The method of claim 1, wherein the benefit agent comprises petrolatum, glyceryl monooleate, or a combination thereof.

4. The method of claim 3, wherein the benefit agent comprises a combination of petrolatum and glyceryl monooleate and the ratio of petrolatum to glyceryl monooleate is about 98:2, by weight of the benefit phase.

5. The method of claim 1, wherein the cleansing composition is applied once per day for 5 days or more.

6. The method of claim 1, wherein the composition comprises from about from about 0.25% to about 1.0%, by weight of the composition, of the zinc pyrithione.

7. The method of claim 1, wherein the anionic surfactant comprises sodium trideceth(n) sulfate, wherein n is from about 0.5 to about 2.7.

8. The method of claim 1, wherein the cleansing phase further comprises from about 0.2% to about 0.8%, by weight of the composition, of a cationic deposition polymer.

9. The method of claim 8, wherein the cationic deposition polymer comprises guar hydroxypropyltrimonium chloride.

10. The method of claim 9, wherein the cationic polymer comprises a cationic charge density of from about 1.0 meq/g to about 1.5 meq/g.

11. A method of treating atopic dermatitis, comprising applying a multi-phase cleansing composition to at least a portion of skin of an individual with atopic dermatitis, wherein the composition comprises a structured cleansing phase comprising from about 3% to about 20%, by weight of the composition, of sodium trideceth(n) sulfate, wherein n is about 2.0, and from about 0.25% to about 5.0%, by weight of the composition, of zinc pyrithione; and from about 1% to about 30%, by weight of the composition, of a benefit phase, comprising from about 1% to about 3% by weight of the composition, of glyceryl monooleate, and from about 5% to about 15%, by weight of the composition, of petrolatum.

12. The method of claim 11, further comprising rinsing the multi-phase cleansing composition from the skin of the individual.

13. The method of claim 12, wherein the ratio of petrolatum to monoglyceryl monooleate is about 98:2, by weight of the benefit phase.

14. The method of claim 13, wherein the cleansing phase further comprises from about 0.2% to about 0.8%, by weight of the composition, of a cationic deposition polymer.

15. The method of claim 14, wherein the cationic polymer comprises a cationic charge density of about 1.0 meq/g to about 1.5 meq/g.

16. The method of claim 15, wherein the composition further comprises from about 0.5% to about 2.5%, by weight of the composition, of a nonionic emulsifier.

17. The method of claim 16, wherein the cationic deposition polymer comprises guar hydroxypropyltrimonium chloride.

18. The method of claim 17, wherein the composition comprises from about 0.25% to about 1.0%, by weight of the composition, of the zinc pyrithione.

* * * * *